(12) United States Patent
Kaye et al.

(10) Patent No.: US 12,315,623 B1
(45) Date of Patent: May 27, 2025

(54) COMPUTING SYSTEM AND METHOD FOR SUPPORTING SELECTIVE PRIORITIZATION

(71) Applicant: McKesson Corporation, Irving, TX (US)

(72) Inventors: Elizabeth Kaye, Suwanee, GA (US); Monique Irmen, Naples, FL (US); Keith Crozier, North Kingstown, RI (US)

(73) Assignee: MCKESSON CORPORATION, Irving, TX (US)

( * ) Notice: Subject to any disclaimer, the term of this patent is extended or adjusted under 35 U.S.C. 154(b) by 232 days.

(21) Appl. No.: 17/029,871

(22) Filed: Sep. 23, 2020

(51) Int. Cl.
| | |
|---|---|
| G16H 40/20 | (2018.01) |
| A61B 17/20 | (2006.01) |
| G06Q 10/10 | (2023.01) |
| G16H 10/60 | (2018.01) |
| G16H 20/10 | (2018.01) |
| G16H 50/20 | (2018.01) |
| G16H 50/30 | (2018.01) |
| G16H 50/50 | (2018.01) |

(Continued)

(52) U.S. Cl.
CPC ............ G16H 40/20 (2018.01); G06Q 10/10 (2013.01); G16H 10/60 (2018.01); G16H 20/10 (2018.01); G16H 50/20 (2018.01); G16H 50/30 (2018.01); G16H 50/50 (2018.01); G16H 50/70 (2018.01); G16H 70/20 (2018.01); *A61B 17/20* (2013.01)

(58) Field of Classification Search
CPC ........ G16H 40/20; G16H 10/60; G16H 20/10; G16H 50/20; G16H 50/30; G16H 50/50; G16H 50/70; G16H 70/20; G06Q 10/10; A61B 17/20
See application file for complete search history.

(56) References Cited

U.S. PATENT DOCUMENTS

| | | | |
|---|---|---|---|
| 8,799,030 B1 * | 8/2014 | Chen ..................... | G16H 20/10 |
| | | | 705/4 |
| 2002/0042726 A1 * | 4/2002 | Mayaud ................. | G06Q 40/08 |
| | | | 705/2 |

(Continued)

OTHER PUBLICATIONS

Schleipman, Arthur Robert. "Health Care Providers Facing Persistent Medication Shortages: Perspectives, Processes, and Policies for Explicit Rationing." Northeastern University, 2017. (Year: 2017).*

*Primary Examiner* — Amber A Misiaszek
(74) *Attorney, Agent, or Firm* — ALSTON & BIRD LLP (57) ABSTRACT

A computing system, method and computer program product selectively prioritize patients for a medical procedure. In relation to a computing system, the computing system includes one or more databases configured to store a plurality of different data sets including a pharmacy and/or medical claims data set, a medication history data set and a patient data set. The computing system also includes processing circuitry configured to access the plurality of different data sets and to analyze the plurality of different data sets in accordance with one or more rule sets. The processing circuitry is further configured to identify a subset of the plurality of patients to be prioritized for the medical procedure as a result of satisfying one or more predefined requirements for the medical procedure based upon an analysis of the plurality of different data sets in accordance with the one or more rule sets.

17 Claims, 3 Drawing Sheets

(51) Int. Cl.
*G16H 50/70* (2018.01)
*G16H 70/20* (2018.01)

(56) References Cited

U.S. PATENT DOCUMENTS

| | | | | |
|---|---|---|---|---|
| 2004/0122709 | A1* | 6/2004 | Avinash | G16H 40/67 |
| | | | | 706/45 |
| 2006/0036619 | A1* | 2/2006 | Fuerst | G16H 50/80 |
| 2008/0103369 | A1* | 5/2008 | Fabius | G16H 80/00 |
| | | | | 600/300 |
| 2008/0183508 | A1* | 7/2008 | Harker | G06Q 10/10 |
| | | | | 705/4 |
| 2009/0089097 | A1* | 4/2009 | Schoenberg | G16H 50/30 |
| | | | | 705/2 |
| 2011/0072381 | A1* | 3/2011 | Gannon | G16H 15/00 |
| | | | | 715/771 |
| 2011/0119212 | A1* | 5/2011 | De Bruin | A61B 5/369 |
| | | | | 706/12 |
| 2013/0204637 | A1* | 8/2013 | Vanderveen | G16H 20/13 |
| | | | | 705/2 |
| 2016/0224734 | A1* | 8/2016 | Ryan | G16H 10/60 |

* cited by examiner

|  | Disease 1 | Disease 2 | Disease 3 | . . . | Disease n |
|---|---|---|---|---|---|
| Medication A | ✓ |  | ✓ |  | ✓ |
| Medication B |  | ✓ |  |  |  |
| Medication C | ✓ |  |  |  |  |
| ⋮ |  |  |  |  |  |
| Code 1 |  | ✓ |  |  |  |
| Code 2 |  |  |  |  | ✓ |
| ⋮ |  |  |  |  |  |
| Patient Identification 1 | ✓ |  |  |  |  |
| Patient Identification 2 |  |  | ✓ |  |  |
| ⋮ |  |  |  |  |  |
| Meds A and D |  |  |  |  | ✓ |
| Meds B, E and G |  | ✓ |  |  |  |
| ⋮ |  |  |  |  |  |
| Med A and then Med X |  |  | ✓ |  |  |
| Med B and then Med Y |  |  |  |  |  |
| ⋮ |  |  |  |  |  |

COMPUTING SYSTEM AND METHOD FOR SUPPORTING SELECTIVE PRIORITIZATION

TECHNOLOGICAL FIELD

An example embodiment relates generally to a computing system, a method and a computer program product configured to support selective prioritization and, more particularly, to a computing system, a method and a computer program product configured to provide for selective prioritization of a patient for a medical procedure.

BACKGROUND

Patients routinely undergo a wide variety of medical procedures including various testing procedures, treatment procedures, vaccinations and the like. Patients generally visit a healthcare provider, such as the patient's primary care physician, a specialist, a testing or treatment facility, a medical clinic, a hospital or the like, to obtain the medical procedure. Once a patient has been identified to be in need of or to benefit from the medical procedure, e.g., once a primary care physician, a specialist or other healthcare provider responsible for the patient's care, determines that the patient should undergo the medical procedure, the patient typically undergoes the medical procedure at a scheduled time or as availability allows after walking into a testing or treatment facility, a medical clinic, a hospital or other healthcare provider.

In some circumstances, however, the availability of a medical procedure is limited with the demand or anticipated demand for a medical procedure exceeding the medical supplies required by and available for the medical procedure. For example, a medical procedure may be limited by the quantity of a particular medication that is available for treatment of or vaccination against a medical condition, by the quantity of medical supplies that are available for testing or treatment of a medical condition or by that is available and/or by the availability of healthcare facilities or personnel that are capable of performing testing or treatment for or vaccination against the medical condition. These limitations in terms of the availability of medication, medical supplies, healthcare facilities or personnel for testing or treatment for or vaccination against a medical condition relative to the demand or anticipated demand for the medical procedure may occur in various instances, but may be exacerbated in an instance in which a medical condition is widespread, either among the population in general or at least in certain segments of the population, and the medication and/or medical supplies required for the medical procedure to test for, treat or vaccinate against the medical condition are being newly developed to address the medical condition or are otherwise limited, such as due to relatively low historical demand.

By way of example, a widespread medical condition, such as a medical condition that may be classified as a pandemic, may be at least partially addressed by testing patients for the medical condition and, if positive, treating the patients for the medical condition. Moreover, once a vaccine has been developed, patients may be vaccinated against the underlying medical condition. As a more specific example, testing patients for and subsequently treating patients who have the coronavirus disease 2019 (COVID-19) would likely limit the spread of the virus by identifying and quarantining individuals who have the virus and facilitating recovery from the virus for those who have the virus. Moreover, once one or more vaccines for COVID-19 have been developed, tested and approved, the vaccination of the population should greatly curb any further spread of the virus.

Because of the widespread nature of a medical condition, such as COVID-19, that is classified as a pandemic, the medical procedures available for testing for and treating the virus may be limited relative to the number of patients who desire testing or treatment. Thus, reliance upon conventional delivery methods for healthcare services may be inefficient as the patients who initially seek the medical procedures for testing, treatment and/or vaccination and who consume the limited resources available for testing, treatment and/or vaccination may not be the patients who are most at risk for more severe complications from the medical condition. In this scenario, at least some of the patients who would be most at risk to suffer more serious consequences from the medical condition, such as at least some of the patients who are most vulnerable to the medical condition, may not be able to obtain the medical procedures since those medical procedures have already been consumed by other patients who are less at risk and less vulnerable to the underlying medical condition. As a result, the deleterious impact of the medical condition upon the population as a whole may be amplified by this failure to allocate limited medical resources, such as for testing, treatment and/or vaccination, to patients who are most at risk and/or most vulnerable to the underlying medical condition.

BRIEF SUMMARY

A computing system, method and computer program product are provided in accordance with an example embodiment in order to selectively prioritize patients for a medical procedure. In this regard, the computing system, method and computer program product of an example embodiment may be configured to identify and prioritize the patients who are most at risk or most vulnerable to a medical condition or who otherwise would most greatly benefit from the medical procedure. Based upon the identification and prioritization of these patients, the limited resources associated with the medical procedures may be made available to or otherwise targeted to these patients. As such, the patients who are most at risk or most vulnerable or who otherwise would obtain the greatest benefit from the medical procedure may have an increased likelihood of obtaining the medical procedures prior to the provision of the medical procedure to other patients who are less at risk or less vulnerable, or who would obtain less benefit from the medical procedures. Consequently, the computing system, method and computer program product of an example embodiment may improve the overall response of a population to a medical condition, such as a widespread medical condition including a medical condition classified as a pandemic, e.g., COVID-19, by allocating the limited medical procedures to test for, treat and/or vaccinate against the underlying medical condition to the subset of the population who are most at risk or most vulnerable and would therefore more likely experience the most severe complications if the medical procedures were unavailable, such as in an instance in which the medical procedures had previously been consumed by other people less at risk or less vulnerable to the medical condition.

In an example embodiment, a computing system is provided that is configured to support selective prioritization of a patient for a medical procedure, such as one or more of a vaccination, a treatment or a testing procedure, in a real-time, near real-time or batch process. The computing system includes one or more databases configured to store a plurality of different data sets. These data sets include a pharmacy and/or medical claims data set that provides information regarding claims submitted on behalf of a plurality of patients. The data sets also include a medication history data set that provides information regarding the medication history of the plurality of patients. The data sets further include a patient data set that provides demographic information for the plurality of patients. The computing system also includes processing circuitry configured to access a plurality of different data sets including the pharmacy and/or medical claims data set, the medication history data set and the patient data set that are stored by the one or more databases. The processing circuitry is also configured to analyze the plurality of different data sets in accordance with one or more rule sets. The processing circuitry is further configured to identify a subset of the plurality of patients to be prioritized for the medical procedure as a result of satisfying one or more predefined requirements for the medical procedure based upon an analysis of the plurality of different data sets in accordance with the one or more rule sets. The computing system further includes a communication interface responsive to the processing circuitry and configured to cause information regarding the prioritization of a respective patient for the medical procedure to be provided at a point of care for the respective patient.

The processing circuitry of an example embodiment is configured to analyze the plurality of different data sets by constructing a disease state confidence matrix to determine the likelihood that a patient has a respective disease based on at least one of the claims submitted on behalf of the patient, the medication history of the patient or healthcare information provided by the patient. In an example embodiment, the one or more predefined requirements that are to be satisfied for a patient to be prioritized for a medical procedure define a plurality of risk levels. Each risk level is defined by a unique combination of the one or more predefined requirements. The processing circuitry of an example embodiment is configured to analyze a plurality of different data sets by identifying a location of a patient based on a location of a pharmacy that has most recently dispensed medication for the patient, at least in an instance in which the location of the pharmacy is distant relative to a home address of the patient as defined by the demographic information of the patient data set.

The processing circuitry of an example embodiment is configured to analyze a plurality of different data sets in accordance with one or more rule sets that are at least partially dependent upon an age of a patient, a disease history of the patient, an occupation of the patient and a location of the patient. In an example embodiment, the processing circuitry is configured to analyze a plurality of different data sets by analyzing diagnosis codes from the claims of the pharmacy and/or medical claims data set to determine that a patient has a respective medical condition. The processing circuitry of an example embodiment is further configured to aggregate information regarding a plurality of patients who have been prioritized for the medical procedure including information regarding locations of the plurality of patients. In this example embodiment, the communication interface is further configured to cause a notification to be provided based at least in part upon the locations of the plurality of patients.

In another example embodiment, a method is provided for supporting selective prioritization of a patient for a medical procedure, such as one or more of a vaccination, a treatment or a testing procedure, in a real-time, near real-time or batch process. The method includes accessing a plurality of different data sets. The data sets include a pharmacy and/or medical claims data set that provides information regarding claims submitted on behalf of a plurality of patients. The data sets also include a medication history data set that provides information regarding the medication history of the plurality of patients. The data sets further include a patient data set that provides demographic information for the plurality of patients. The method also includes analyzing the plurality of different data sets in accordance with one or more rule sets. The method further includes identifying a subset of a plurality of patients to be prioritized for the medical procedure as a result of satisfying one or more predefined requirements for the medical procedure based upon an analysis of the plurality of different data sets in accordance with the one or more rule sets. Additionally, the method includes causing information regarding the prioritization of a respective patient for the medical procedure to be provided at a point of care for the respective patient.

The method of an example embodiment analyzes the plurality of different data sets by constructing a disease state confidence matrix to determine a likelihood that a patient has a respective disease based on at least one of the claims submitted on behalf of the patient, the medication history of the patient or healthcare information provided by the patient. In an example embodiment, the one or more predefined requirements that are to be satisfied to prioritize a patient for the medical procedure define a plurality of risk levels. Each risk level is defined by a unique combination of the one or more predefined requirements. The method of an example embodiment analyzes the plurality of different data sets by identifying a location of a patient based on a location of the pharmacy that has most recently dispensed medication for the patient, at least in an instance in which the location of the pharmacy is distant relative to a home address of the patient as defined by the demographic information of the patient data set.

The method of an example embodiment analyzes the plurality of different data sets in accordance with one or more rule sets and at least partially dependent upon an age of the patient, a disease history of the patient, an occupation of the patient and a location of the patient. In an example embodiment, analyzing the plurality of different data sets includes analyzing diagnosis codes from the claims of the pharmacy and/or medical claims data set to determine that a patient has a respective medical condition. The method of an example embodiment also includes aggregating information regarding a plurality of patients who have been prioritized for the medical procedure including information regarding locations of the plurality of patients. The method of this example embodiment also includes causing a notification to be provided based at least in part upon the locations of the plurality of patients.

In a further example embodiment, a computer program product is provided that is configured to support selective prioritization of a patient for a medical procedure, such as one or more of a vaccination, a treatment or a testing procedure, in a real-time, near real-time or batch process. The computer program product includes at least one non-transitory computer-readable storage medium having computer-executable program code portions stored thereon with the computer-executable program code portions including program code instructions configured to access a plurality of different data sets. The data sets include a pharmacy and/or medical claims data set that provides information regarding claims submitted on behalf of a plurality of patients. The data sets also include a medication history data set that provides information regarding the medication history of the plurality of patients. The data sets further include a patient data set that provides demographic information for the plurality of patients. The computer-executable program code portions also include program code instructions configured to analyze the plurality of different data sets in accordance with one or more rule sets. The computer-executable program code portions further include program code instructions configured to identify a subset of the plurality of patients to be prioritized for the medical procedure as a result of satisfying one or more predefined requirements for the medical procedure based upon an analysis of the plurality of different data sets in accordance with one or more rule sets. The computer-executable program code portions additionally include program code instructions configured to cause information regarding the prioritization of a respective patient from the medical procedure to be provided at a point of care for the respective patient.

The program code instructions configured to analyze the plurality of different data sets include, in an example embodiment, program code instructions configured to construct a disease state confidence matrix to determine a likelihood that a patient has a respective disease based on at least one of the claims submitted on behalf of the patient, the medication history of the patient or healthcare information provided by the patient. In an example embodiment, the one or more predefined requirements that are to be satisfied to prioritize a patient for the medical procedure define a plurality of risk levels. Each risk level is defined by a unique combination of the one or more predefined requirements. In an example embodiment, the program code instructions configured to analyze the plurality of different data sets include program code instructions configured to identify a location of a patient based on a location of a pharmacy that has most recently dispensed medication for the patient, at least in an instance in which the location of the pharmacy is distant relative to a home address of the patient as defined by the demographic information of the patient data set.

The program code instructions configured to analyze the plurality of different data sets include, in an example embodiment, program code instructions configured to analyze the plurality of different data sets in accordance with one or more rule sets that are at least partially dependent upon an age of a patient, a disease history of the patient, an occupation of the patient and a location of the patient. The program code instructions configured to analyze the plurality of different data sets include, in an example embodiment, program code instructions configured to analyze diagnosis codes from the claims of the pharmacy and/or medical claims data set to determine that a patient has a respective medical condition. In an example embodiment, the computer-executable program code portions further include program code instructions configured to aggregate information regarding a plurality of patients who have been prioritized for the medical procedure including information regarding locations of the plurality of patients. The computer-executable program code portions of this example embodiment also include program code instructions configured to cause a notification to be provided based at least in part upon the locations of the plurality of patients.

BRIEF DESCRIPTION OF THE DRAWINGS

Having thus described certain embodiments of the invention in general terms, reference will now be made to the accompanying drawings, which are not necessarily drawn to scale, and wherein:

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

A computing system, method and computer program product are provided in accordance with an example embodiment in order to support the selective prioritization of a patient for a medical procedure. The computing system, method and computer program product may be configured to support prioritization of a patient for any of a variety of medical procedures. By way of example, however, the computing system, method and computer program product will be described hereinafter in conjunction with the prioritization of a patient for a medical procedure for which the requisite supplies are limited or anticipated to be limited relative to the likely demand for the medical procedure. In this regard, the requisite supplies for a medical procedure may include a medication, e.g., a prescription drug, that is utilized for testing for, treatment of or vaccination against the medication condition, medical supplies that are required for testing for, treatment of or vaccination against the medication condition and/or healthcare providers, healthcare facilities and/or other equipment that are utilized to administer the medical procedure.

The medical procedure for which a patient is selectively prioritized may be any of a plurality of different types of medical procedures. For example, the medical procedure may be a testing procedure to identify if a patient has or is at risk for a particular medical condition. Additionally or alternatively, the medical procedure may be a treatment procedure, such as a treatment procedure that relies upon prescription medicine, specialized equipment, specialized personnel or the like, in order to increase the likelihood of recovery from the medical condition and/or to improve the rate at which the patient recovers from the medical condition, to reduce the complications experienced by the patient following recovery from the medical condition and to at least partially alleviate the symptoms experienced by the patient while recovering from the medical condition. Additionally or alternatively, the medical procedure may be a vaccination in which a patient is vaccinated against the medical condition.

The medical condition for which the medical procedure relates may also be any of a wide variety of medical conditions, such as a medical condition that is anticipated to create a demand for the supplies required for the related medical procedure to test for, treat or vaccinate against the medical procedure that will exceed the availability of the supplies. For example, the medical condition may be a widespread medical condition that impacts or potentially impacts a significant percentage of the overall population, thereby leading to substantial demand for the related medical procedure. Alternatively, the medical condition may be a novel or a relatively new and emerging medical condition for which medical procedures are also being newly developed. By way of example, but not of limitation, the medical condition may be a medical condition that is both widespread, such as to classified as a pandemic, and novel such that there is substantial demand for the medical procedures to test for, treat and vaccinate against the medical condition with supplies required for those medical procedures, such as the prescription medications and other medical supplies, being limited in terms of availability. One example of a medical condition for which patients may be selectively prioritized to receive a medical procedure, such as a testing procedure, a treatment procedure and/or a vaccination, is COVID-19 that has the potential to impact a very large portion of the world's population and for which medical procedures including the prescription medication, medical supplies and medical equipment required for testing and treatment have at times been in limited supply. Moreover, one or more vaccines are currently under development with respect to COVID-19 and are anticipated to be in limited supply relative to the substantial demand that is expected following development, testing and approval of the vaccine(s).

Figure 1:
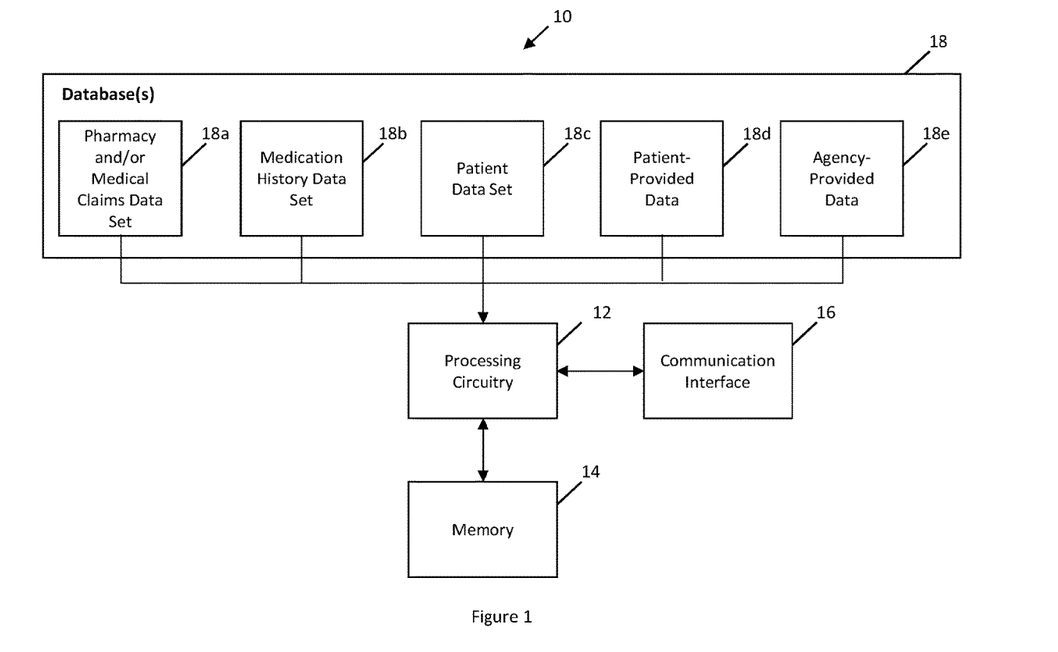
FIG. 1 is a block diagram of a computing system that may be specifically configured in accordance with an example embodiment of the present disclosure.

The computing system that is configured to support selective prioritization of a patient for a medical procedure may be embodied by any of a wide variety of different types of computers. For example, the computing system may be embodied by the server, a computer workstation, a personal computer, a distributed network of computers or other computer resources, etc. Regardless of the manner in which the computing system is embodied, however, the computing system 10 of an example embodiment includes processing circuitry 12, a communication interface 14 and optionally a memory 16, such as shown in FIG. 1.

In some embodiments, the processing circuitry 12 (and/or co-processors or any other processors assisting or otherwise associated with the processing circuitry) can be in communication with the memory 16 via a bus for passing information among components of the computing system 10. The memory can be non-transitory and can include, for example, one or more volatile and/or non-volatile memories. In other words, for example, the memory may be an electronic storage device (for example, a computer readable storage medium) comprising gates configured to store data (for example, bits) that can be retrievable by a machine (for example, a computing device like the processing circuitry). The memory can be configured to store information, data, content, applications, instructions, or the like for enabling the apparatus to carry out various functions in accordance with an example embodiment of the present disclosure. For example, the memory can be configured to buffer input data for processing by the processing circuitry. Additionally or alternatively, the memory can be configured to store instructions for execution by the processing circuitry.

The processing circuitry 12 can be embodied in a number of different ways. For example, the processing circuitry may be embodied as one or more of various hardware processing means such as a processor, a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processing circuitry can include one or more processing cores configured to perform independently. Alternatively, the processing circuitry can include one or more processors configured in tandem via the bus to enable independent execution of instructions.

In an example embodiment, the processing circuitry 12 can be configured to execute instructions stored in the memory 16 or otherwise accessible to the processing circuitry. Alternatively or additionally, the processing circuitry can be configured to execute hard coded functionality. As such, whether configured by hardware or software methods, or by a combination thereof, the processing circuitry can represent an entity (for example, physically embodied in circuitry) capable of performing operations according to an embodiment of the present disclosure while configured accordingly. Thus, for example, when the processing circuitry is embodied as an ASIC, FPGA or the like, the processing circuitry can be specifically configured hardware for conducting the operations described herein. Alternatively, as another example, when the processing circuitry is embodied as an executor of software instructions, the instructions can specifically configure the processing circuitry to perform the algorithms and/or operations described herein when the instructions are executed. However, in some cases, the processing circuitry can be a processor of a specific device, e.g., a specific type of computing system, configured to employ an embodiment of the present disclosure by further configuration of the processor by instructions for performing the algorithms and/or operations described herein. The processing circuitry can include, among other things, a clock, an arithmetic logic unit (ALU) and/or one or more logic gates configured to support operation of the processing circuitry.

The computing system 10 of an example embodiment can also include the communication interface 14 that can be any means such as a device or circuitry embodied in either hardware or a combination of hardware and software that is configured to receive and/or transmit data from/to other electronic devices in communication with the computing system, such as electronic devices associated with one or more patients, one or more healthcare providers, one or more healthcare facilities, various governmental agencies, one or more insurance plans or third party payers, or the like. Additionally or alternatively, the communication interface can be configured to communicate in accordance with various wireless protocols including Global System for Mobile Communications (GSM), such as but not limited to Long Term Evolution (LTE). In this regard, the communication interface can include, for example, an antenna (or multiple antennas) and supporting hardware and/or software for enabling communications with a wireless communication network. In this regard, the communication interface can include, for example, an antenna (or multiple antennas) and supporting hardware and/or software for enabling communications with a wireless communication network. Additionally or alternatively, the communication interface can include the circuitry for interacting with the antenna(s) to cause transmission of signals via the antenna(s) or to handle receipt of signals received via the antenna(s). In some environments, the communication interface can alternatively or also support wired communication.

As described below, the computing system 10 of FIG. 1 may also include one or more databases 18 configured to store a plurality of different data sets. In this regard, the one or more databases may be co-located with the processing circuitry 12 and/or the communication interface 14 or the one or more databases may be remote from, but in communication with the processing circuitry and/or the communication interface. As shown, the processing circuitry 12 of the illustrated embodiment is in communication with the one or more databases so as to access the data stored by the plurality of different data sets. The processing circuitry may be configured to directly communicate with the one or more databases or to communicate with the one or more databases via the communication interface 14. Although depicted in FIG. 1 and described hereinafter as being a component of the computing system, the computing system of another example embodiment is configured to communicate with one or more databases that are external to the computing system, but in communication therewith, such as via a communications network.

The one or more databases 18 may include a variety of different data sets which provide information regarding the patient and the medical history of the patient and from which the risk level of the patient with respect to the medical condition may be determined, such as in a probabilistic manner. As shown in FIG. 1, the one or more databases include a pharmacy and/or medical claims data set 18a that provides information regarding claims submitted on behalf of a plurality of patients to one or a plurality of pharmacies or chains of pharmacies. In this regard, the pharmacy and/or medical claim data set may include pharmacy claims submitted by or on behalf of patients to a payor, such as an insurance company or other third party payor, for prescription medication and other medical supplies that are dispensed to a patient by a pharmacy. The pharmacy and/or medical claims data set may also include information regarding medical claims submitted by or on behalf of one or more patients seeking coverage from a payor, such as an insurance company or other third party payor, for medical procedures that the patient has undergone or prescription medication dispensed to the patient that is covered by a medical insurance plan, as opposed to a pharmacy insurance plan, of the patient. In an example embodiment, the pharmacy and/or medical claims data set includes information regarding claims submitted on behalf of a plurality of patients to a plurality of different payors, such as a plurality of different insurance companies or other third-party payors. Thus, in an instance in which a patient has a plurality of insurance plans, either concurrently or over the course of time, the information regarding claims submitted on behalf of the patient to each of the plurality of different third-party payors will provide a more complete medical history for the patient.

As also shown in FIG. 1, the one or more databases 18 include a medication history data set 18b that provides information regarding the medication history of the plurality of patients. The medication history data set may be obtained from any of a wide variety of patient records including electronic health records of the plurality of patients. These patient records may be provided by a plurality of different healthcare providers including healthcare providers associated with a plurality of different healthcare systems. Some of the information included in the patient records may be duplicative with the information gleaned from the claims submitted on behalf of the patient and included within the pharmacy and/or medical claims data set. For example, the information regarding a prescription medication that is prescribed by a healthcare provider to a patient and for which a patient seeks reimbursement by submitting a claim for the prescription medication may appear both in the patient records for which information is stored in the medication history data set and in the claims submitted on behalf of a patient for the prescription medication for which information is stored in the pharmacy and/or medical data set. However, other information from the patient records will not appear within the claims data of the pharmacy and/or medical claims data set. For example, information regarding non-prescription medication that a healthcare provider indicates that a patient should take may be recorded in the patient records, but not the claims data since a claim for the non-prescription medication may not be submitted. As another example, the patient may pay for prescription medication or medical supplies in such a manner, such as in cash, such that a claim for the prescription medication or medical supplies will not be submitted and the information for the prescription medication or medical supplies will be recorded in the patient records, but not in the claims data.

Further, the one or more databases 18 of the computing system 10 of FIG. 1 include a patient data set 18c that provides demographic information for the plurality of patients. A wide variety of demographic information may be provided for the plurality of patients. For example, the demographic information may include information regarding the sex of the patient, the age of the patient and the home address of the patient, information regarding the medical history of the patient and/or family members of the patient, etc. The patient data set may be provided by the patient and/or by one or more healthcare providers and/or healthcare systems that have treated the patient in the past and that have collected the demographic information in conjunction with such treatment.

Other data sets that may be optionally included include a patient-provided data set 18d and an agency-provided data set 18e. The patient provided data set may include information provided by the patient as to one or more medical conditions that the patient has experienced in the past. The agency-provided data set may provide information provided by a healthcare-related agency, such as the Centers for Disease Control (CDC) or one or more testing agencies.

Although a plurality of different data sets are described herein, the one or more databases 18 may also be configured to store additional and/or different data sets relating to the patient and the medical history of the patient. The inclusion of a plurality of different data sets within the one or more databases including, for example, the pharmacy and/or medical claims data set 18a, the medication history data set 18b and the patient data set 18c and optionally the patient-provided data set 18d and the agency-provided data set 18e provide a rich and substantial data set relating to the patient and the medical history of the patient to increase the accuracy of a probabilistic determination as to the risk level of a patient with respect to a medical condition with the risk level, in turn, informing the prioritization of the patient for a medical procedure associated with the medical condition, thereby leading to greater confidence in the resulting prioritization of a patient for a medical procedure.

Figure 2:
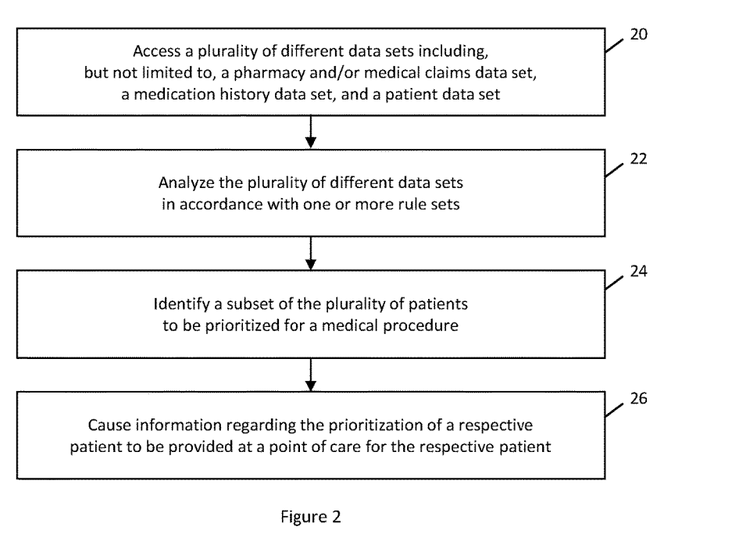
FIG. 2 is a flowchart illustrating operations performed, such as by the computing system of FIG. 1, in accordance with an example embodiment of the present disclosure.

Referring now to FIG. 2, the operations performed, such as by the computing system 10, in order to support the selective prioritization of a patient for a medical procedure are depicted. As shown in block 20, the computing system includes means, such as the processing circuitry 12, the one or more databases 18 or the like, configured to access a plurality of different data sets. The plurality of different data sets that are accessed include the pharmacy and/or medical claims data set 18a, the medication history data set 18b and a patient data set 18c. Additional data sets may also be accessed including the patient-provided data set 18d, the agency-provided data set 18e or other data sets. As shown in block 22, the computing system also includes means, such as the processing circuitry or the like, configured to analyze a plurality of different data sets in accordance with one or more rule sets. This analysis may be performed in a variety of different manners in order to identify the patients who are most at risk or most vulnerable to a medical condition or who are anticipated to benefit most greatly from a medical procedure associated with the medical condition.

A patient may be considered to be at risk or vulnerable to a medical condition in a variety of different manners. For example, a patient may be considered to be at risk or to be vulnerable to a medical condition in an instance in which the risk of death or significant complications for the patient is substantial, such as by having been experienced by at least a predefined percentage of similarly situated patients who have contracted the medical condition. Additionally or alternatively, the risk or vulnerability of a patient may be defined in terms of one or more of the anticipated length of time required for recovery if the patient should contract the medical condition, the likelihood that the patient will need to be hospitalized if the patient should contract the medical condition, the severity of the symptoms likely to be experienced by the patient if the patient should contract the medical condition and go untreated, etc. Additionally, the benefit that is anticipated to be experienced by a patient to a medical procedure associated with a medical condition may be defined in different manners including a different likely outcome experienced by a patient who undergoes the medical procedure, such as the likely survival of a patient contracting a medical condition, either in general or without permanent significant complications. Additionally or alternatively, the benefit that is anticipated to be experienced by a patient to a medical procedure associated with a medical condition may be defined in terms of one or more of the anticipated rate of recovery of the patient, an anticipated reduction in the severity of symptoms experienced by the patient during the recovery from the medical condition, etc.

The computing system 10, such as the processing circuitry 12, may be configured to analyze a plurality of different data sets in a variety of different manners. In an example embodiment, the computing system, such as the processing circuitry, is configured to analyze a plurality of different data sets in accordance with one or more rule sets that are at least partially dependent upon a plurality of different parameters, such as the age of the patient, the disease history of the patient and, in some embodiments, the location of the patient. For example, certain medical conditions may more greatly impact patients of certain ages, such as younger patients, older patients, etc., and to cause those patients, on average, more substantial complications such that the age of the patient may be at least partially determinative in relation to the anticipated response of the patient to contracting the medical condition. The computing system, such as the processing circuitry, may be configured to determine the age of the patient based upon demographic information for the patient provided by the patient data set 18c.

The disease history of the patient may also impact the anticipated outcome of the patient in response to contracting the medical condition. As used herein, a disease experienced by a patient may be any of a plurality of different medical conditions experienced by the patient. For example, patients who have had one or more diseases, such as particular forms of cancer, diabetes, chronic obstructive pulmonary disease (COPD), etc., may be more susceptible to a medical condition or may have a less successful anticipated outcome if the patient were to contract the medical condition. In some embodiments, the computing system, such as the processing circuitry, is configured to determine the disease history of a patient from the patient data set 18c and/or the patient-provided data set 18d. For example, these data sets may identify one or more diseases, such as one or more medical conditions, with which a patient has been diagnosed.

Additionally or alternatively, the disease history of a patient may be inferred from the medication history and/or the claims data associated with a patient, even in an instance in which the patient has not been diagnosed with a disease. In this regard, the computing system 10, such as the processing circuitry 12, may be configured to determine the disease history of the patient based upon the medication history of the patient as provided by the medication history data set 18b and/or information regarding claims submitted on behalf of the patient as provided by the pharmacy and/or medical claims data set 18a.

The disease history of a patient may be determined from the medication history and/or the claims data associated with a patient in various manners. In one example embodiment, the computing system 10, such as the processing circuitry 12, is configured to analyze the plurality of different data sets by analyzing diagnosis codes from the claims of the pharmacy and/or medical claims data set 18a to determine that a patient has a respective medical condition. Examples of diagnosis codes include, but are not limited to, CPT and ICD-10 codes.

Figure 3:
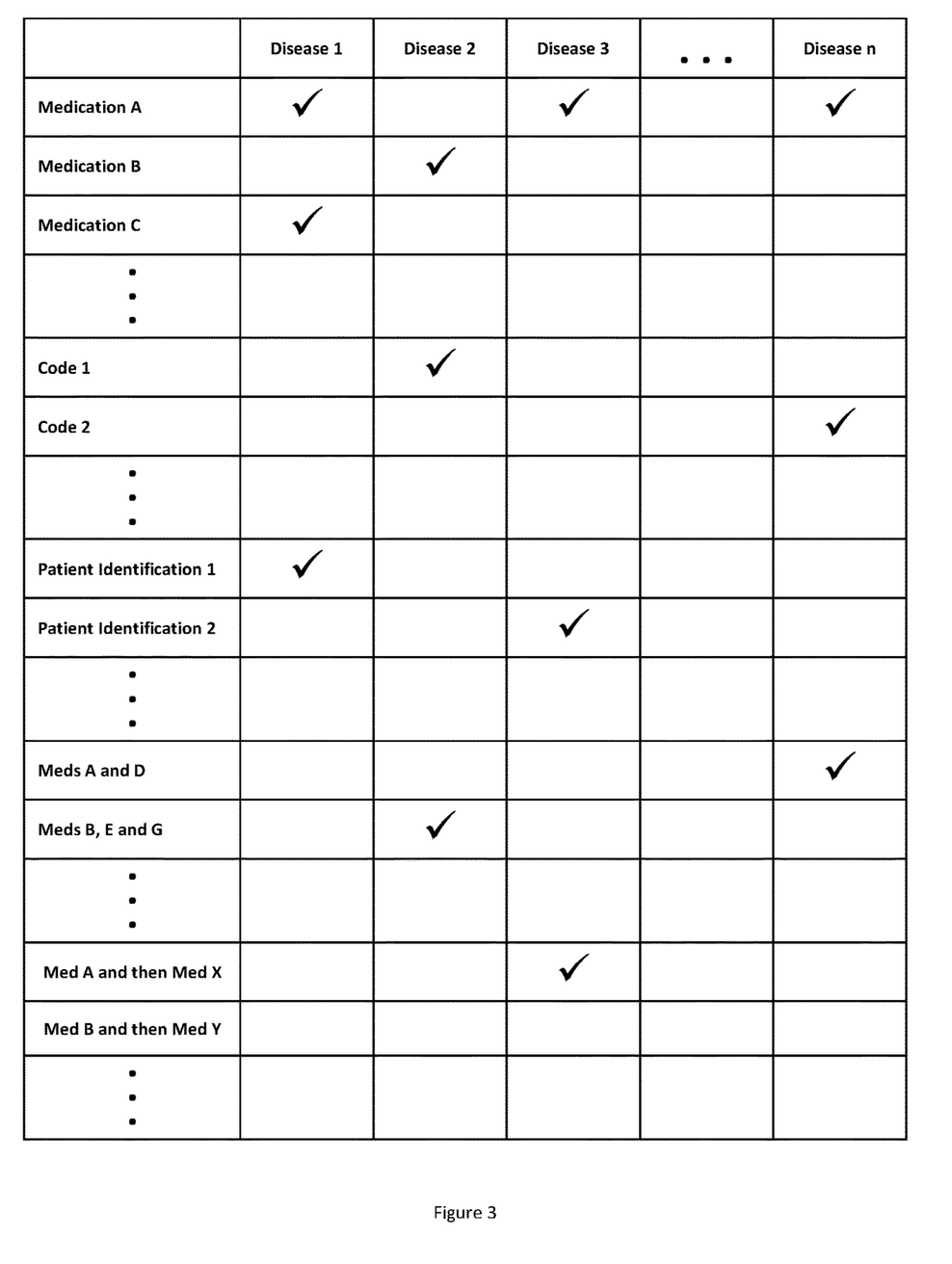
FIG. 3 is an example of a disease state confidence matrix that may be constructed and utilized to determine a likelihood that a patient has a respective disease in accordance with an example embodiment of the present disclosure.

In a more general example embodiment, the computing system 10, such as the processing circuitry 12, is configured to analyze the plurality of different data sets by constructing a disease state confidence matrix to determine a likelihood that a patient has or is at risk for a respective disease based at least upon one or more of the claims submitted on behalf of the patient and/or the medication history of the patient. In an example embodiment, a patient may be considered to be at risk for a respective disease in an instance in which the patient is determined to have a risk level that equals or exceeds a predefined threshold. The disease state confidence matrix is configured to determine the probability that a patient has or is at risk for one or more of a plurality of different diseases based upon the medications that have been prescribed for the patient in the past and optionally also based upon other healthcare information that is instructive as to the risk level of the patient for one or more different diseases. In this regard, some medications are very specific in regard to treatment of a specific disease, while other medications are utilized in a more generic manner to treat a plurality of different diseases. Thus, the disease state confidence matrix that is constructed may more greatly weight the contributions of the medications that are prescribed for treatment of one or a small number of diseases than those medications that are prescribed more generally for the treatment of a plurality of different diseases and which are therefore less dispositive of the disease experienced by a patient. Additionally, different combinations of medications and/or different sequences of medications may also be utilized by the disease state confidence matrix that is constructed in order to define the likelihood that a patient has or is at risk for a respective disease since different combinations of medications and/or different sequences of medications are utilized to treat different diseases.

As to the other healthcare information that may be considered by the disease state confidence matrix, any healthcare information that is at least partly determinative in regard to whether a patient has or is at risk for a respective disease may be considered. Examples of other types of healthcare information that may be considered by the disease state confidence matrix are the various codes utilized by patient records, claims, etc. that identify a diagnosis, a procedure that the patient is to undergo. Examples of the codes (referenced as Code 1 and Code 2 in FIG. 3) include diagnosis codes, such as International Classification of Diseases (ICD-10) codes and Current Procedural Terminology (CPT) codes. Other examples of healthcare information that may be considered by the disease state confidence matrix include information provided by the patient (referenced in FIG. 3 as Patient Identification 1 and Patient Identification 2 in FIG. 3) in relation to one or more medical conditions that the patient has experienced in the past.

Thus, the resulting disease state confidence matrix defines one or more medications and/or other healthcare information, one or more combinations of medications and/or other healthcare information, or one or more sequences of medications that may be prescribed in order to treat a respective disease. By comparing the medications that have been prescribed for the patient over time to information regarding the medications utilized to treat different diseases as defined by the disease state confidence matrix and by optionally also taking into consideration other types of healthcare information, the likelihood that a patient has or is at risk for one or more of the respective diseases for which the disease state confidence matrix is constructed may be identified and utilized in conjunction with the potential prioritization of the patient for a medical procedure as described below.

One example of a disease state confidence matrix that is provided by way of example, but not of limitation, is depicted in FIG. 3. As shown, the disease state confidence matrix provides a columnar listing of a plurality of different medications and other healthcare information, different combinations of medications and different sequences of medications, while a plurality of different diseases are listed in a row. The matrix of this example includes checkmarks in the column underlying a respective disease for those medications and other healthcare information, those combinations of medications or those sequences of medications that, in combination, are indicative of the respective disease. The medications that have been prescribed for a patient and optionally the other healthcare information may then be compared to the disease state confidence matrix and in an instance in which the patient has been prescribed all of the medications, including any combinations of medications or sequences of medications, that are associated with a respective disease and also in an instance in which the medications, combinations of medications or sequences of medications are unique for the respective disease, the computing system 10, such as the processing circuitry 12, of this example embodiment is configured to determine that the patient has a high likelihood of having or being at risk for the respective disease, particularly in an instance in which any other healthcare information that is considered is also indicative of the patient having or being at risk for the respective disease. Conversely, in an instance in which a patient has none or a very small number (such as less than a predefined number or less than a predefined percentage) of the medications, including any combinations of medications or sequences of medications, that are associated with a respective disease, the computing system, such as the processing circuitry, of this example embodiment is configured to determine that the patient has a low likelihood of having or being at risk for the respective disease, particularly in an instance in which any other healthcare information that is considered is also indicative of the patient not having and not being at risk for the respective disease. In some instances, the presence of a medication in a patient's medical history may be a contraindication of the patient having or being at risk for a respective disease. In other words, if a patient has been prescribed a respective medication, the patient likely does not have and is likely not at risk for a respective disease since the medication is contraindicative of the respective disease. Although not shown, the disease state confidence matrix may therefore not only include positive correlations between a medication and a respective disease state, but also negative correlations, e.g., contraindications, between a medication and a respective disease state and may take those positive and negative correlations into account in relation to determining the likelihood of a patient having or being at risk for a respective disease. Further, in an instance in which a patient has been prescribed less than all, but more than the very small number of the medications, including any combinations of medications or sequences of medications, that are associated with a respective disease, the computing system, such as the processing circuitry, of this example embodiment is configured to determine that the patient has a medium or moderate likelihood of having the respective disease.

In addition to the age of the patient and the disease history of the patient, the location of the patient may also be instructive in relation to determining the risk or vulnerability of a patient to a medication condition and, as a result, whether the patient should be prioritized in relation to a medical procedure associated with the medical condition. In this regard, the prevalence of a medical condition may not be geographically uniform. Instead, patients in certain regions may be more likely to contract the medical condition than patients in other regions. As such, the location of a patient in these situations in which the geographic dispersion of a medical condition is widely variable may also be at least partially definitive with respect to the likelihood that a patient will contract the medical condition. As noted above, the demographic information for a patient provided by the patient data set 18c may include the home address of a patient. In some instances, this home address of the patient may be utilized to define the location of the patient.

In some circumstances, however, a patient may not be located at their home address, at least not during the period of time in which the patient is considered for prioritization of a medical procedure associated with a medical condition. For example, a patient may be staying with a relative or a friend located in a different region and may not return to their home address during the relevant period of time, either because the patient does not desire to return to their home address or because of travel restrictions that may have been implemented during a pandemic or that are attributable to an infirmity of the patient. Alternatively, the patient may have been away from their home address, such as for business or personal travel, and may be required to remain at their current location, different than their home address, due to travel restrictions imposed during a pandemic. Regardless of the reason, in these circumstances in which the current location of the patient is distant from the home address of the patient, the location of the patient that is relevant with respect to the determination of the likelihood of a patient contracting the medical condition and therefore relevant to the determination of the prioritization of a patient for a medical procedure associated with a medical condition is not the home address of the patient, but, the current address. In this example embodiment, the current location of the patient is considered distant from the home address of the patient in an instance in which the current location of the patient differs from the home address by more than a predefined distance, such as a predefined distance selected such that the patient is determined to be resident in a different city or a different state. In an example embodiment, the predefined distance is defined to be that distance for which the likelihood of contracting the medical condition varies by at least a material amount, such as a predefined percentage.

In an instance in which the current address of the patient is distant from the home address of the patient, the computing system 10 of an example embodiment, such as the processing circuitry 12, is configured to identify the location of a patient, such as the current location of a patient, based on a location of a pharmacy that has most recently dispensed medication for the patient, at least in an instance in which the location of the pharmacy is distant, such as more than a predefined distance from, the home address of the patient as defined by the demographic information of the patient data set 18c. The location of the pharmacy that has most recently dispensed medication for the patient may be provided by the medication history of the patient or by the information regarding claims submitted on behalf of a patient.

Although the age of the patient, the disease history of the patient and, in some embodiments, the location of the patient have been described above in relation to parameters of the data set that are analyzed in relation to the prioritization of a patent, other parameters may additionally or alternatively be analyzed. For example, the computing system 10, such as the processing circuitry 12, may be configured to additionally or alternatively analyze the occupation or job class of a patient, such as may be provided by the patient data set 18c. In this example embodiment, patients have certain occupations, such as first responders and/or healthcare workers, may be identified for prioritization relative to patients having other occupations.

As noted above, the computing system 10, such as the processing circuitry 12, analyzes the different data sets for data associated with a respective patient including, for example, at least the age, disease history and location of the patient. In an example embodiment, the computing system, such as the processing circuitry, is configured to analyze the plurality of different data sets in accordance with one or more rule sets. The rule sets define different combinations of data associated with a patient that are indicative of the patient being more likely or less likely to be at risk or vulnerable to the medical condition or to benefit more greatly from a medical procedure associated with the medical condition.

In the example embodiment in which the age of the patient, the disease history of the patient and the location of the patient are analyzed, the one or more rule sets may define different combinations of the age of the patient, the disease states of the patient, the occupation of the patient and the location of the patient that cause the patient to be more likely or less likely to be at risk or vulnerable to the medical condition or to benefit more greatly from a medical procedure associated with the medical condition. For example, the rule set may define a patient who is 65 years or older and who has had one or both of a first disease or a second disease to have an elevated risk of suffering significant complications if the patient were to contract a medical condition, regardless of the location of the patient. The rule sets may also define a patient who is 65 years of age or older and who is currently located in a certain region having a relatively high incidence level of a medical condition to have an elevated risk with respect to the medical condition, regardless of the disease history of the patient. Still further, the rule sets of this example embodiment may define any patient, regardless of age or location, who has had a particular disease to have an elevated risk with respect to the medical condition.

Still further, the rule set may define certain combinations of data to indicate that a patient has a relatively low risk associated with the medical condition. For example, a patient who is 50 years of age or younger and who has not had any one of a plurality of predefined diseases and who is not located within one or more predefined regions, such as one or more predefined regions having high incidence levels of a medical condition, may be identified to have a relatively low risk or at least a lower risk of contracting the medical condition and, if contracted, of suffering serious complications.

Turning now to block 24 of FIG. 2, the computing system 10 of an example embodiment includes means, such as the processing circuitry 12 or the like, configured to identify a subset of a plurality of patients to be prioritized for the medical procedure as a result of satisfying one or more predefined requirements for the medical procedure based upon an analysis of the plurality of different data sets in accordance with the one or more rule sets. In some example embodiments, the one or more predefined requirements define a plurality of risk levels associated with the medical condition. Each risk level may be defined by a unique combination of the one or more predefined requirements. In an example embodiment, the risk levels may be defined to range from a high risk level identifying that subset of patients for which contracting the medical condition poses a high risk to a low risk level for those patients for which contracting the medical condition poses a low risk and one or more intermediate risk levels for those patients for which contracting the medical condition poses a moderate level of risk between the high risk level and the low risk level.

A variety of different predefined requirements may be utilized in conjunction with the prioritization of a patient for the medical procedure and, in some embodiments, in conjunction with the definition of the plurality of risk levels. For example, different combinations of various parameters related to the patient such as the age of the patient, the disease state of the patient, including one or more medical conditions experienced by the patient, and the location of the patient may be considered in relation to determining the risk level and/or the prioritization of the patient for a medical procedure. As noted above, the occupation of a patent may also be considered in conjunction with prioritization in some embodiments.

The computing system 10, such as the processing circuitry 12, of an example embodiment may be configured to identify the subset of the plurality of patients to be prioritized for a medical procedure in various manners. For example, the computing system, such as the processing circuitry, may be configured to identify the subset of patients to be prioritized for a medical procedure to be those patients that satisfy the predefined requirements. Alternatively, in an embodiment in which a plurality of risk levels are defined, the computing system, such as the processing circuitry, may be configured to identify the subset of patients to be prioritized for the medical procedure to be those patients having the highest risk level, but none of the other patients in an instance in which the medical procedures (such as the medication, medical supplies or medical facilities required by the medical procedure) are very limited in supply. Alternatively, the computing system, such as the processing circuitry, may be configured to identify the patients having a high risk level as well as patients having an intermediate risk level to be prioritized for a medical procedure in other instances in which the medical procedures (such as the medication, medical supplies or medical facilities required by the medical procedure) are only somewhat limited in supply.

As shown in block 26 of FIG. 2, the computing system 10 of an example embodiment also includes means, such as the processing circuitry 12, the communication interface 16 or the like, configured to cause information regarding the prioritization of a respective patient for a medical procedure to be provided at a point of care for the respective patient. In this regard, the point of care may be that point at which the patient is interacting with their physician or other healthcare provider, that point in time at which the patient is interacting with a pharmacist to obtain a prescribed medication or that point in time in which the patient is interacting with the plan of a payor, such as an insurance provider or other third party payor, in order to seek reimbursement or payment for a medical procedure. By providing information regarding prioritization of the respective patient for the medical procedure at the point of care, the likelihood of the patient receiving the notification that they have been prioritized for the medical procedure and then gaining an understanding as to the steps to be taken to avail themselves of the medical procedure are increased, thereby further increasing the likelihood of a successful outcome. The computing system, such as the processing circuitry, may be configured to identify the subset of the plurality of patients to be prioritized for the medical procedure in a batch process. However, in order to provide for the information regarding prioritization of a respective patient for the medical procedure to be provided at the point of care, the computing system, such as the processing circuitry, of an example embodiment is configured to identify the subset of the plurality of patients to be prioritized for the medical procedure in a timely manner, such as in real time or near real time, with respect to the initial inquiry as to the relative prioritization of the patient which, in turn, may have been made at the point of care, such as by the physician or pharmacist during interaction with the patient or by the plan in conjunction with the submission of a claim. Thus, although the data represented by the plurality of data sets 18 may be collected over time, such as in one or more batch processes, the identification of the subset of patients to be prioritized for a medical procedure may be performed in real time or near real time, such as while the patient is at a point of care.

As described above, the computing system 10, method and computer program product of an example embodiment utilize a plurality of different datasets that are provided by a plurality of different sources, such as claims data, medication history data, patient data and the like. By utilizing a rich dataset that is substantial in quantity and originates from a plurality of different sources, the dataset that is analyzed in order to selectively prioritize one or more patients for a medical procedure allows for more accurate and targeted identification of the patients who are selectively prioritized. Consequently, the patients may be prioritized for the medical procedure in a more accurate manner and a more targeted manner. Thus, the information that is provided at the point of care for a respective patient regarding the prioritization of a respective patient may be more accurate and focused, thereby increasing or maximizing the use of the communication network for the delivery of the information and reducing the network consumption that would otherwise have been consumed to provide information to other patients who would have been potentially errantly prioritized for the medical procedure in instances in which less fulsome datasets were analyzed in order to prioritize patients for the medical procedure.

Not only does the computing system 10, method and computer program product conserve the limited communication network resources and therefore provide a technical advantage, but the computing system, method and computer program product of an example embodiment conserve the healthcare resources that will be expended to treat the patients and to provide the medical procedure by increasing the likelihood that the patients prioritized for the medical procedure and for whom the healthcare resources are expended have been accurately identified by use of the richer dataset. Consequently, the expenditure of healthcare resources for patients who have been errantly prioritized as may otherwise occur more frequently if less fulsome datasets were analyzed for purposes of the selective prioritization may be avoided.

The computing system 10, method and computer program product of an example embodiment may be configured to identify one or more individual patients for prioritization with respect to a medical procedure associated with a medical condition for which the one or more individual patients are at greater risk or more vulnerable. However, the computing system, method and computer program product of an example embodiment may be configured to also determine aggregated information on a larger segment of the patient population and to provide a notification based upon the aggregated information. As described below, this information may be utilized for various purposes including planning purposes, scheduling purposes, inventory management including inventor supply and deployment purposes as well as other logistical purposes and the like.

In this example embodiment, the computing system 10 includes means, such as the processing circuitry 12 or the like, configured to aggregate information regarding a plurality of patients who have been prioritized for the medical condition including information regarding locations of a plurality of patients. See block 30 of FIG. 4. The computing system, such as the processing circuitry, of this example embodiment may be configured to aggregate information for all patients, for patients within one or more respective regions or for some other group of patients. By way of example, the computing system, such as the processing circuitry, of an example embodiment may be configured to aggregate information regarding the plurality of patients that have been prioritized for the medical procedure and who are located within a particular state, who are members of a particular insurance plan, who are employees of a particular employer, who are patients of a particular medical practice, or the like. The computing system, such as the processing circuitry, of this example embodiment may be configured to aggregate a variety of different types of information including information regarding the number or percentage of patients who have been prioritized for the medical procedure at each of a plurality of different locations, the number of patients that have been prioritized for the medical procedure and who have been identified to be at each of the different risk levels, etc.

The computing system 10 of this example embodiment also includes means, such as the processing circuitry 12, the communication interface 16 or the like, configured to cause a notification to be provided based at least in part upon the locations of the plurality of patients who have been prioritized for the medical procedure for which information has been aggregated. See block 32 of FIG. 4. The notifications may be provided to a variety of different recipients for any of a variety of purposes.

Figure 4:
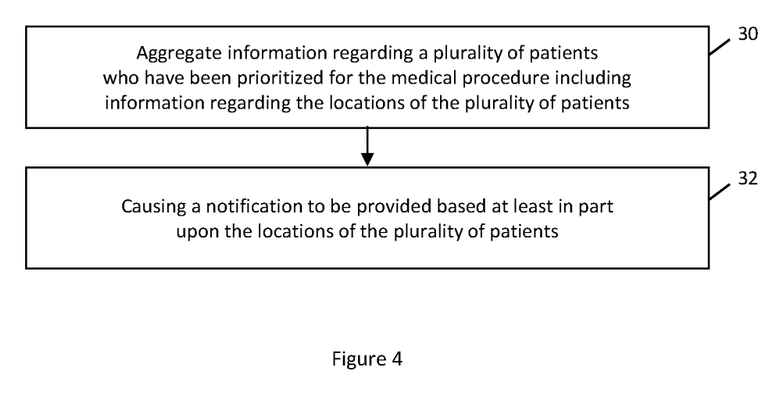
FIG. 4 is a flowchart illustrating operations performed, such as by the computing system of FIG. 1, in order to cause notifications to be provided based upon aggregated information regarding a plurality of patients who have been prioritized for a medical procedure in accordance with an example embodiment of the present disclosure.

For example, notifications may be provided to pharmacies or pharmacy chains regarding the number of patients prioritized for the medical procedure for whom medication is dispensed at a respective pharmacy. As such, the pharmacies or chains of pharmacies may utilize the aggregated information regarding the patients who have been prioritized for the medical procedure for inventory management purposes, such as to stock an appropriate quantity of medication or other medical supplies so as to have the requisite medication or other medical supplies on hand for the patients who have been prioritized for the medical procedure.

The notification provided in accordance with this example embodiment may also be provided to the federal, state or local government or to various governmental agencies and may be utilized for a wide variety of purposes including tracking the spread of the medical condition and the impact of containment efforts. The aggregated information may therefore assist with the planning of a coordinated response to the medical condition. In a similar manner to a pharmacy or a chain of pharmacies but potentially on a larger scale, the notification provided to the government or a governmental agency may facilitate inventory or supply management such that the requisite medications and medical supplies for a medical procedure are redirected to those locations for which a plurality of patients have been prioritized for the medical procedure in an effort to ensure that the patients prioritized for the medical procedure have better access to the requisite medication and medical supplies utilized by the medical procedure.

Still further, the computing system 10, such as the processing circuitry 12, may be configured to provide notifications to healthcare providers and/or healthcare systems of the patients of the healthcare provider or healthcare system that have been prioritized for a medical procedure. As such, the healthcare providers or healthcare system may develop a plan for treating their patients who have been prioritized for the medical procedure. In this regard, a healthcare provider or a healthcare system that has a larger number of patients prioritized for the medical procedure may schedule the healthcare provider and/or the availability of healthcare resources or facilities in such a manner as to treat or respond to the plurality of patients who have been prioritized for the medical procedure.

Additionally or alternatively, the computing system 10, such as the processing circuitry 12, may be configured to notify insurance plans or other third-party payors of the patients who are members of the insurance plan or third-party payor and how have been prioritized for the medical procedure. As such, the insurance plan or other third-party payor may correspondingly develop a strategy for supporting the patients seeking the medical procedure and, in some instances, may communicate with the patients in an effort to ensure that the patients receive the appropriate medical procedures, but do so in the most cost effective manner.

Although certain examples of the notifications that may be provided in accordance with this example embodiment have been provided, the computing system 10, method and computer program product of this example embodiment may provide notifications regarding the aggregated information for the plurality of patients who have been prioritized for a medical procedure to any of a wide variety of other parties and/or for any of a wide variety of purposes. As described above in relation to block 26 of FIG. 2, notifications or other information may be provided to the patients who have been prioritized for the medical procedure, thereby allowing the patients to schedule the medical procedure and to otherwise take precautions to avoid the spread of the medical condition to others.

As noted above, FIGS. 2 and 4 are flowcharts illustrating the operations performed by a computing system, method and computer program product, such as computing system 10 of FIG. 1, in accordance with one embodiment of the present invention. It will be understood that each block of the flowcharts, and combinations of blocks in the flowcharts, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory 16 of a computing system employing an embodiment of the present invention and executed by the processing circuitry 12. As will be appreciated, any such computer program instructions may be loaded onto a computer or other programmable apparatus (e.g., hardware) to produce a machine, such that the resulting computer or other programmable apparatus provides for implementation of the functions specified in the flowchart blocks. These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks. As such, the operations of FIGS. 2 and 4, when executed, convert a computer or processing circuitry into a particular machine configured to perform an example embodiment of the present invention. Accordingly, the operations of FIGS. 2 and 4 define an algorithm for configuring a computer or processing circuitry, e.g., processor, to perform an example embodiment. In some cases, a general purpose computer may be provided with an instance of the processor which performs the algorithm of FIGS. 2 and 4 to transform the general purpose computer into a particular machine configured to perform an example embodiment.

Accordingly, blocks of the flowcharts support combinations of means for performing the specified functions and combinations of operations for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions. In some embodiments, certain ones of the operations above may be modified or further amplified and additional optional operations may be included. It should be appreciated that each of the modifications, optional additions or amplifications below may be included with the operations above either alone or in combination with any others among the features described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A computing system configured to support selective prioritization of a patient for a medical procedure based on: (i) one or more of a real-time process or a near real-time process in addition to (ii) one or more batch processes, the computing system comprising:
    one or more databases configured to store a plurality of different data sets that are collected over time in the one or more batch processes from a plurality of different sources, the plurality of different data sets including one or more of a pharmacy claims data set or a medical claims data set that provides information regarding claims submitted on behalf of a plurality of patients, a medication history data set that provides information regarding the medication history of the plurality of patients and a patient data set that provides demographic information for the plurality of patients;
    processing circuitry configured to:
        access the plurality of different data sets including one or more of the pharmacy claims data set or the medical claims data set, the medication history data set and the patient data set that are collected over time in the one or more batch processes and stored by the one or more databases,
        analyze the plurality of different data sets in accordance with one or more rule sets by analyzing diagnosis codes from the claims of one or more of the pharmacy claims data set or the medical claims data set to determine that a patient has a medical condition; and
        perform one or more of the real-time process or the near real-time process to identify a subset of the plurality of patients to be prioritized for the medical procedure as a result of satisfying one or more predefined requirements for the medical procedure based upon an analysis of the plurality of different data sets in accordance with the one or more rule sets, wherein the subset of the plurality of patients to be prioritized is identified in real time or near real time with respect to an inquiry as to a relative prioritization of a respective patient that is made at a point of contact for the respective patient; and
    a communication interface responsive to the processing circuitry and configured to cause information regarding the prioritization of the respective patient for the medical procedure to be delivered via a communication network and provided in real-time or near real-time at the point of care for the respective patient in a manner that conserves limited communication network resources by increasing use of the communication network for delivery of the information regarding the prioritization of the respective patient for the medical procedure while reducing network consumption of the communication network with respect to information otherwise provided for patients that have not been prioritized, and wherein the communication interface is configured to cause a notification to be provided to the respective patient regarding the prioritization of the respective patient by causing the information regarding the prioritization of the respective patient to be provided to the point of care that includes the respective patient and one of a healthcare provider, a pharmacist or a payor and to cause a notification to be pushed to a pharmacy or a pharmacy chain regarding a number of patients prioritized for the medical procedure for whom medication is to be dispensed at a respective pharmacy to facilitate stocking of the medication for the patients who have been prioritized for the medical procedure.

2. A computing system according to claim 1 wherein the processing circuitry is configured to analyze the plurality of different data sets by constructing a disease state confidence matrix to determine a likelihood that a patient has a respective disease based on at least one of the claims submitted on behalf of the patient, the medication history of the patient or healthcare information provided by the patient.

3. A computing system according to claim 1 wherein the one or more predefined requirements define a plurality of risk levels, and wherein each risk level is defined by a unique combination of the one or more predefined requirements.

4. A computing system according to claim 1 wherein the processing circuitry is configured to analyze the plurality of different data sets by identifying a location of a patient based on a location of a pharmacy that has most recently dispensed medication for the patient at least in an instance in which the location of the pharmacy is distant relative to a home address of the patient as defined by the demographic information of the patient data set.

5. A computing system according to claim 1 wherein the processing circuitry is configured to analyze the plurality of different data sets by analyzing the plurality of different data sets in accordance with one or more rule sets that are at least partially dependent upon an age of a patient, a disease history of the patient, an occupation of the patient and a location of the patient.

6. A computing system according to claim 1 wherein the processing circuitry is further configured to aggregate information regarding a plurality of patients who have been prioritized for the medical procedure including information regarding locations of the plurality of patients, and wherein the communication interface is further configured to cause a notification to be provided based at least in part upon the locations of the plurality of patients.

7. A computing system according to claim 1 wherein the medical procedure is one or more of a vaccine, a treatment or a testing procedure.

8. A method for supporting selective prioritization of a patient for a medical procedure based on: (i) one or more of a real-time process or a near real-time process in addition to (ii) one or more batch processes, the method comprising:
    accessing a plurality of different data sets that are collected over time in the one or more batch processes from a plurality of different sources and that include one or more of a pharmacy claims data set or a medical claims data set that provides information regarding claims submitted on behalf of a plurality of patients, a medication history data set that provides information regarding the medication history of the plurality of patients and a patient data set that provides demographic information for the plurality of patients;
    analyzing the plurality of different data sets in accordance with one or more rule sets by analyzing diagnosis codes from the claims of one or more of the pharmacy claims data set or the medical claims data set to determine that a patient has a respective medical condition;

performing one or more of the real-time process or the near real-time process to identify a subset of the plurality of patients to be prioritized for the medical procedure as a result of satisfying one or more predefined requirements for the medical procedure based upon an analysis of the plurality of different data sets in accordance with the one or more rule sets, wherein the subset of the plurality of patients to be prioritized is identified in real time or near real time with respect to an inquiry as to a relative prioritization of a respective patient that is made at a point of contact for the respective patient;

causing information regarding the prioritization of the respective patient for the medical procedure to be provided by a communication interface and delivered via a communication network in real-time or near real-time to the point of care for the respective patient in a manner that conserves limited communication network resources by increasing use of the communication network for delivery of the information regarding the prioritization of the respective patient for the medical procedure while reducing network consumption of the communication network with respect to information otherwise provided for patients that have not been prioritized; and cause a notification to be provided to the respective patient regarding the prioritization of the respective patient by causing the information regarding the prioritization of the respective patient to be provided to the point of care that includes the respective patient and one of a healthcare provider, a pharmacist or a payor and cause a notification to be pushed to a pharmacy or a pharmacy chain regarding a number of patients prioritized for the medical procedure for whom medication is to be dispensed at a respective pharmacy to facilitate stocking of the medication for the patients who have been prioritized for the medical procedure.

9. A method according to claim 8 wherein analyzing the plurality of different data sets comprises constructing a disease state confidence matrix to determine a likelihood that a patient has a respective disease based on at least one of the claims submitted on behalf of the patient, the medication history of the patient or healthcare information provided by the patient.

10. A method according to claim 8 wherein the one or more predefined requirements define a plurality of risk levels, and wherein each risk level is defined by a unique combination of the one or more predefined requirements.

11. A method according to claim 8 wherein analyzing the plurality of different data sets comprises identifying a location of a patient based on a location of a pharmacy that has most recently dispensed medication for the patient at least in an instance in which the location of the pharmacy is distant relative to a home address of the patient as defined by the demographic information of the patient data set.

12. A method according to claim 8 wherein analyzing the plurality of different data sets comprises analyzing the plurality of different data sets in accordance with one or more rule sets that are at least partially dependent upon an age of a patient, a disease history of the patient, an occupation of the patient and a location of the patient.

13. A method according to claim 8 further comprising:
aggregating information regarding a plurality of patients who have been prioritized for the medical procedure including information regarding locations of the plurality of patients; and
causing a notification to be provided based at least in part upon the locations of the plurality of patients.

14. A method according to claim 8 wherein the medical procedure is one or more of a vaccine, a treatment or a testing procedure.

15. A computer program product configured to support selective prioritization of a patient for a medical procedure based on: (i) one or more of a real-time process or a near real-time process in addition to (ii) one or more batch processes, the computer program product comprising at least one non-transitory computer-readable storage medium having computer-executable program code portions stored therein, the computer-executable program code portions comprising program code instructions configured to:

access a plurality of different data sets that are collected over time in the one or more batch processes from a plurality of different sources and that include one or more of a pharmacy claims data set or a medical claims data set that provides information regarding claims submitted on behalf of a plurality of patients, a medication history data set that provides information regarding the medication history of the plurality of patients and a patient data set that provides demographic information for the plurality of patients;

analyze the plurality of different data sets in accordance with one or more rule sets by analyzing diagnosis codes from the claims of one or more of the pharmacy claims data set or the medical claims data set to determine that a patient has a respective medical condition;

perform one or more of the real-time process or the near real-time process to identify a subset of the plurality of patients to be prioritized for the medical procedure as a result of satisfying one or more predefined requirements for the medical procedure based upon an analysis of the plurality of different data sets in accordance with the one or more rule sets, wherein the subset of the plurality of patients to be prioritized is identified in real time or near real time with respect to an inquiry as to a relative prioritization of a respective patient that is made at a point of contact for the respective patient;

cause information regarding the prioritization of the respective patient for the medical procedure to be provided by a communication interface and delivered via a communication network in real-time or near real-time to the point of care for the respective patient in a manner that conserves limited communication network resources by increasing use of the communication network for delivery of the information regarding the prioritization of the respective patient for the medical procedure while reducing network consumption of the communication network with respect to information otherwise provided for patients that have not been prioritized; and cause a notification to be provided to the respective patient regarding the prioritization of the respective patient by causing the information regarding the prioritization of the respective patient to be provided to the point of care that includes the respective patient and one of a healthcare provider, a pharmacist or a payor and cause a notification to be pushed to a pharmacy or a pharmacy chain regarding a number of patients prioritized for the medical procedure for whom medication is to be dispensed at a respective pharmacy to facilitate stocking of the medication for the patients who have been prioritized for the medical procedure.

16. A computer program product according to claim 15 wherein the program code instructions configured to analyze the plurality of different data sets comprise program code instructions configured to construct a disease state confidence matrix to determine a likelihood that a patient has a respective disease based on at least one of the claims submitted on behalf of the patient, the medication history of the patient or healthcare information provided by the patient.

17. A computer program product according to claim 15 wherein the program code instructions configured to analyze the plurality of different data sets comprise program code instructions configured to identify a location of a patient based on a location of a pharmacy that has most recently dispensed medication for the patient at least in an instance in which the location of the pharmacy is distant relative to a home address of the patient as defined by the demographic information of the patient data set.

\* \* \* \* \*